United States Patent
Ramin et al.

(10) Patent No.: US 6,352,963 B2
(45) Date of Patent: *Mar. 5, 2002

(54) MAKE-UP REMOVING COMPOSITION

(75) Inventors: Roland Ramin, Paris; Pascal Arnaud, L'Hay les Roses, both of (FR)

(73) Assignee: L'Oreal, S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/141,346

(22) Filed: Aug. 27, 1998

(30) Foreign Application Priority Data

Aug. 28, 1997 (FR) .............................. 97 10757

(51) Int. Cl.$^7$ .............................................. A61K 7/047
(52) U.S. Cl. ..................................................... 510/118
(58) Field of Search ................................ 510/118, 121, 510/136; 424/401, 61, 70.21, 70.22, 70.31

(56) References Cited

U.S. PATENT DOCUMENTS

| 4,712,571 A | * | 12/1987 | Remz et al. |
| 5,063,049 A | * | 11/1991 | Billings |
| 5,071,639 A | | 12/1991 | Soyama et al. ............... 424/61 |
| 5,093,108 A | * | 3/1992 | Pappas et al. |
| 5,342,536 A | * | 8/1994 | Miner et al. ................ 252/162 |
| 5,435,994 A | * | 7/1995 | Valenty |
| 5,468,417 A | * | 11/1995 | LeGrow ................ 252/174.15 |
| 5,543,085 A | * | 8/1996 | Miner ........................ 510/118 |
| 5,741,766 A | * | 4/1998 | Marion et al. ............. 510/130 |

FOREIGN PATENT DOCUMENTS

| DE | 195 22 750 | 1/1997 |
| DE | 776 665 | 6/1997 |
| EP | 281 360 | 9/1993 |
| EP | 455 073 | 11/1994 |
| EP | 651 990 | 5/1995 |
| EP | 705 592 | 4/1996 |
| EP | 708 114 | 4/1996 |
| EP | 776 654 | 6/1997 |
| EP | 0 781 780 | 7/1997 |
| EP | 0795321 | * 9/1997 |
| FR | 1 453 089 | 9/1966 |
| GB | 2 021 411 | 12/1979 |
| WO | 94 18935 | 9/1994 |
| WO | 96 02225 | 1/1996 |

OTHER PUBLICATIONS

Hawley, G. G., The Condensed Chemical Dictionary, 10th Ed., Van Nostrand Reinhold Co., New York, 1981, pp. 115, 159, 308, 296, 297, 316, 317, 335, 358, 68, 390, 422, 433, 435, 436, 581, 582, 583, 665, 666, 678, 679, 682, 863, 1100, 1101.*

English Language Derwent Abstract of RD 95 378 007, 1995.

Majewicz et al., "Oil–Based Cosmetic and Therapeutic Compositions Containing Ethylguar", Research Disclosure, No. 37807, p. 642, XP–002067837, Oct. 1995, Hercules Incorporated.

Clarke et al., "Ethyl Galactomannan Film Properties For Use In Personal Care Applications", Research Disclosure, No. 38413, pp. 235–236, XP–002067847, Apr. 1996, Hercules Incorporated.

English Language Derwent Abstract of DE 195 22 750, 1997.

English Language Derwent Abstract of EP A 651 990, 1995.
English Language Derwent Abstract of EP A 705 592, 1996.
English Language Derwent Abstract of EP A 776 665, 1997.
English Language Derwent Abstract of FR 1 453 089, 1966.

* cited by examiner

Primary Examiner—Diana Dudash
Assistant Examiner—Alysia Berman
(74) Attorney, Agent, or Firm—Finnegan, Henderson, Farabow, Garrett & Dunner, LLP

(57) ABSTRACT

A composition for removing make-up from keratinous material comprised of a polysaccharide alkyl ether formed of units containing at least two different saccharide rings, each unit containing at least one hydroxyl group substituted with a saturated hydrocarbon-based alkyl chain combined with a make-up-removing system comprising at least one non-aqueous solvent and/or an oil and/or a surfactant. The polysaccharide alkyl ether preferably has a molecular weight of greater than 200,000 and is in particular a guar gum alkyl ether having a degree of substitution of about 2 to 3, in particular 2.5.

24 Claims, No Drawings

MAKE-UP REMOVING COMPOSITION

Applicants reference herein the patent applications of ROLAND RAMIN for Ser. No. 09/141,515 entitled THICKENED FILM-FORMING COMPOSITION and PASCAL ARNAUD for Ser. No. 09/141,514 entitled THICKENED COMPOSITION COMPRISING FUSED SILICA both filed on even date herewith and incorporate the disclosures thereof specifically by reference herein.

The present invention relates to make-up-removing compositions and to the use, for the preparation of a composition and/or in a composition for removing make-up from keratinous material, of a polysaccharide alkyl ether combined with a make-up-removing system. In particular, this composition is intended for removing make-up from keratinous material such as the nails, the eyelashes, the eyebrows, the hair and the skin (cheeks, forehead, neck, eyelids).

The compositions conventionally used for removing make-up from keratinous material are generally in the form of a lotion or a milk. In addition, they contain oils and/or surfactants which allow the make-up to be removed. Such a composition is described in particular in patent application EP-A-705,592.

Although very effective, these known compositions have a certain number of drawbacks. In particular, they are often difficult to take up and can run between the fingers.

In order to thicken the compositions, it is known to add a thickener to the composition. When the composition mainly comprises a non-aqueous phase, i.e. the composition comprises either an organic solvent or an oil, a thickener of lipophilic nature is used, in a known manner. Thus, a clay such as bentonite can be used, for example, to thicken a fatty phase, but this clay has the drawback of making the thickened composition opaque.

It is also known to use fused silica to thicken a non-aqueous phase, but the compositions thus thickened have a tendency to be translucent.

In addition, these thickeners of lipophilic nature are only compatible with a limited number of solvents and oils commonly used in make-up-removing products, thus limiting the variety of formulations of these compositions.

There is a need to have available a make-up-removing product in more or less fluid, gelled form which has both transparency properties and good rheology.

The inventors have observed that this aim can be achieved by using, as thickener, a specific polysaccharide alkyl ether in a make-up-removing composition. This thickener makes it possible to prepare make-up-removing compositions in gelled form which can be transparent. These gelled compositions moreover have good rheology, which can range from a fluid texture to a thick texture, according to the manufacturer's wishes.

In addition, this thickener is compatible with many solvents and oils, thus allowing a wide variety of solvents and oils to be used in the make-up-removing compositions and allowing novel cosmetic products to be envisaged.

A subject of the invention is thus the use, for the preparation of a composition and/or in a composition for removing make-up from keratinous material, of a polysaccharide alkyl ether formed of units containing at least two different saccharide rings, each unit containing at least one hydroxyl group substituted with a saturated hydrocarbon-based alkyl chain combined with a make-up-removing system comprising at least one non-aqueous solvent and/or an oil.

In the thickener according to the invention, the term "hydrocarbon-based alkyl chain" is understood to refer to a linear or branched chain preferably containing from 1 to 24, more preferably from 1 to 10, better still from 1 to 6 and more especially from 1 to 3, carbon atoms. In particular, the alkyl chain is selected from ethenyl and propenyl and preferably saturated chains and in particular methyl, ethyl, n-propyl, isopropyl, n-butyl, isobutyl, tert-butyl and n-pentyl. These alkyl ethers can be manufactured as described in documents EP-A-281,360 and EP-A-708,114, the disclosures of which are specifically incorporated by reference herein.

According to a preferred embodiment of the invention, the polysaccharide alkyl ether has a weight-average molecular weight preferably of greater than 100,000, and more preferably greater than 200,000. This molecular weight can be up to 1 million. This alkyl ether can preferably contain from one to six, and better still from two to four, hydroxyl groups per unit, substituted with a saturated or unsaturated hydrocarbon-based alkyl chain.

The saccharide rings are selected in particular from mannose, galactose, glucose, furanose, rhamnose and arabinose.

According to a preferred embodiment of the invention, the polysaccharide alkyl ether is an alkyl ether of a gum and more particularly of a gum which is nonionic overall, i.e. one which contains few or no ionic groups. As appropriate gums, mention may be made, for example, of guar gum, in which the unit comprises a galactose and a mannose, carob gum, in which the unit comprises a galactose and a mannose, karaya gum, which is a complex mixture of rhamnose, galactose and galacturonic acid, and gum tragacanth, which is a complex mixture of arabinose, galactose and galacturonic acid.

According to a preferred embodiment of the invention, the polysaccharide alkyl ether is a guar gum derivative. Thus, advantageously, the alkyl ether is preferably an alkyl galactomannan with a $C_1$ to $C_6$, and better still $C_1$ to $C_3$, alkyl chain and more particularly ethyl guar having a degree of substitution of from 2 to 3 and in particular from about 2.5 to 2.8, as described in the documents RD 95378007 (October 1995) and EP-A-708,114, the disclosures of which are specifically incorporated herein by reference. This gum is in particular that sold by the company Aqualon under the names N-HANCE-AG 200® and N-HANCE AG 50®.

The concentration of alkyl ether depends on the desired pharmaceutical form and consistency for the make-up-removing composition. In particular, the weight ratio of the amount of solvent and/or of oil to the amount of thickener is selected, for example, in the range preferably from 5 to 1000. The composition according to the invention can contain, for example, an amount of polysaccharide alkyl ether preferably ranging from 0.1 to 20% of the total weight of the composition, more preferably from 2% to 8% by weight and better still from 3% to 6% by weight.

According to the invention, the expression make-up-removing system is understood to refer to a compound or a mixture of compounds having the property of removing the make-up present on keratinous material.

The make-up-removing system can comprise at least one non-aqueous solvent (or said organic solvent) or at least one make-up-removing oil or at least one surfactant, or mixtures thereof.

The make-up-removing system is selected depending on the nature of the make-up to be removed.

According to a first embodiment of the invention, the make-up-removing system can comprise at least one organic solvent. This solvent can be selected in particular from:

ketones that are liquid at room temperature, such as methyl ethyl ketone, methyl isobutyl ketone, diisobutyl ketone, isophorone, cyclohexanone and acetone;

alcohols that are liquid at room temperature, such as ethanol, isopropanol, diacetone alcohol, 2-butoxyethanol and cyclohexanol;

glycols that are liquid at room temperature, such as ethylene glycol, propylene glycol and pentylene glycol;

propylene glycol ethers that are liquid at room temperature, such as propylene glycol monomethyl ether, propylene glycol monomethyl ether acetate and dipropylene glycol mono-n-butyl ether;

esters with a short chain, (having from 3 to 8 carbon atoms in total), such as ethyl acetate, methyl acetate, propyl acetate, n-butyl acetate and isopentyl acetate;

ethers that are liquid at room temperature, such as diethyl ether, dimethyl ether and dichlorodiethyl ether;

alkanes that are liquid at room temperature, such as decane, heptane, dodecane and cyclohexane;

aromatic cyclic compounds that are liquid at room temperature, such as toluene and xylene;

aldehydes that are liquid at room temperature, such as benzaldehyde and acetaldehyde.

Esters and ketones having not more than 10 carbon atoms are more preferably used, and more particularly methyl ethyl ketone, ethyl acetate, methyl acetate or butyl acetate.

The solvents can be present in a proportion preferably of from 0 to 99.9% by weight, relative to the total weight of the composition, and better still from 20% to 98% by weight.

These solvents are more particularly suitable for removing make-up from the nails: in this case, the composition constitutes a nail varnish dissolver.

Thus, another subject of the invention is a nail varnish dissolver containing at least one solvent selected from methyl isobutyl ketone, diisobutyl ketone, isophorone, cyclohexanone, isopropanol, diacetone alcohol, 2-butoxyethanol, cyclohexanol, methyl acetate, propyl acetate, n-butyl acetate, isopentyl acetate, diethyl ether, dimethyl ether, dichlorodiethyl ether, decane, dodecane, cyclohexane, xylene, benzaldehyde and acetaldehyde.

According to a second embodiment of the invention, the make-up-removing system can comprise at least one make-up-removing oil. As make-up-removing oils, mention may be made in particular of:

linear or branched hydrocarbons of mineral or synthetic origin, such as liquid petroleum jelly, isohexadecane, isododecane, squalane and equivalents;

fatty acid esters, and in particular esters having a total number of carbon atoms ranging preferably from 12 to 38 and better still from 12 to 20, in particular the esters obtained from a straight- or branched-chain alcohol having from 1 to 17 carbon atoms and from a straight- or branched-chain fatty acid having from 8 to 36 carbon atoms, and better still from 8 to 18 carbon atoms.

The ester used as make-up-removing oil can be selected, in particular, from the group consisting of dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate and isononyl isononanoate.

The oil can be present in a proportion preferably of from 0 to 99.9% by weight, relative to the total weight of the composition, and better still from 20% to 98% by weight.

According to a third embodiment of the invention, the make-up-removing system can further comprise at least one surfactant. This make-up-removing system comprises one or more surfactants having a make-up-removing action.

The surfactant can be of the anionic, nonionic or amphoteric type, but preferably of the nonionic type. Among the nonionic surfactants, those particularly preferred are:

polyoxyethylenated fatty alcohols, such as the product sold under the name "REMCOPAL 21912 AL" by the company Gerland, polyoxyethylenated alkylphenols, such as the product sold under the name "TRITONx100" by the company Rohm & Haas, and condensates of ethylene oxide and of propylene oxide, such as those sold under the name "SYNPERONIC PE" by the company ICI, and in particular those with the reference numbers L 31, L 64, F 38, F 88, L 92, P 103, F 108 and F 127.

Among the anionic surfactants, mention may be made in particular of:

alkyl ether sulphates, such as the product sold under the name "TEXAPON ASV" by the company Henkel, alkyl sulphoacetates, such as the products sold under the name "LATHANOL LAL" by the company Stepan, alkyl sulphosuccinates, such as the product sold under the name "SODIUM DIOCTYL SULPHOSUCCINATE" by the company Rhône-Poulenc, alkylamido sulphosuccinates, such as the product sold under the name "REWODERM S 1333" by the company Rewo, alkylamido polypeptides, such as the product sold under the name "LAMEPON S" by the company Grunau, and acyl sarcosinates, such as the product sold under the name "ORAMIX L 30" by the company SEPPIC.

Among the amphoteric surfactants, mention may be made in particular of:

alkylamidopropyldimethylbetaines, such as the product sold under the name "TEGOBETAINE L 7" by the company Goldschmidt, alkylamidobetaines, such as the product sold under the name "INCRONAM 30" by the company Croda, imidazoline derivatives, such as the product sold under the name "CHIMEXANE HD" by the company Chimex, and N-alkyl-β-iminodipropionates, such as the product sold under the name "MONATERIC ISA 35" by the company Mona.

The surfactant can be present in a proportion preferably of from 0 to 10% by weight, relative to the total weight of the composition, and better still from 0.5% to 5% by weight.

When the make-up-removing system comprises a make-up-removing oil and/or a surfactant, the make-up-removing composition is particularly suitable for removing make-up from the eyes (eyelids, eyelashes and eyebrows) and from the face (forehead, cheeks, neck), as well as for removing make-up from the hair.

Thus, another subject of the invention is a product for removing make-up from the eyes and/or the face and/or the hair, comprising at least one make-up-removing oil selected from the group formed by isododecane, squalane, fatty acid esters having a total number of carbon atoms ranging from 12 to 38, except for isopropyl palmitate, isopropyl myristate, 2-ethylhexyl palmitate, 2-octyldodecyl stearate, 2-octyldodecyl erucate, isostearyl isostearate and 2-octyldodecyl benzoate, and/or at least one make-up-removing surfactant.

When the make-up-removing system comprises at least one surfactant, it is normally desirable for the make-upremoving system to contain either at least one non-aqueous solvent or at least one oil in order to allow the make-up-removing composition to be thickened with the polysaccharide alkyl ether defined above. In this case, the oil can be a make-up-removing oil or an oil conventionally used in the cosmetics or dermatological field, referred to as a complementary oil.

Moreover, these complementary oils can also be added to the make-up-removing system when this system comprises no surfactants.

Among the non-make-up-removing complementary oils, mention may be made of:
- fatty alcohols such as 2-octyldodecanol;
- silicone oils, in particular of low viscosity (preferably less than 100 cst at 25° C.), such as linear or branched polysiloxanes with a low degree of polymerization, for instance methylpolysiloxane, methylphenylpolysiloxane, ethylmethylpolysiloxane, ethylphenylpolysiloxane, hydroxymethylpolysiloxane, alkylpolydimethylsiloxane and cyclic polysiloxanes such as octamethylcyclopentasiloxane and decamethylcyclopentasiloxane, or mixtures thereof;
- oils of mineral, animal or synthetic origin, for example hydrogenated polyisobutenes;
- oils of plant origin, such as liquid triglycerides, for example sunflower oil, corn oil, soybean oil, marrow oil, grapeseed oil, sesame oil, hazelnut oil, apricot oil, macadamia oil, castor oil and caprylic/capric acid triglycerides such as those sold by the company Stearineries Dubois or those sold under the names MIGLYOL 810, 812 and 818 by the company Dynamit Nobel.

These non-make-up-removing complementary oils are preferably used in concentrations ranging from 0 to 50% of the total weight of the composition, and more preferably from 0 to 40%.

A gelled composition resulting from the combination of the polysaccharide alkyl ether and the make-up-removing system, as defined above, can be used as it is and can itself constitute a composition for removing make-up from keratinous material. It can also be incorporated into a more complex formulation for removing make-up from keratinous material, in an effective amount to obtain both the desired texture and viscosity, and good removal of make-up from the keratinous material.

These complementary oils are preferably used in concentrations preferably ranging from 0 to 50% by weight, and more preferably from 0 to 40% by weight, relative to the total weight of the gel phase.

In addition, an aqueous phase can preferably be added, in an amount ranging from 0.1 to 30% by weight relative to the total weight of the composition, and better still from 5% to 10% by weight.

They can also contain conventional adjuvants such as dyes, fragrances, preserving agents, sunscreens and moisturizers. These adjuvants are present in amounts preferably ranging from 0 to 20% by weight relative to the weight of the composition.

The invention also relates to a process for removing make-up from keratinous material, characterized in that an effective amount of a composition containing a gel formed from a polysaccharide alkyl ether and from a make-up-removing system comprising a non-aqueous solvent and/or an oil, as defined above, is applied to the surface of the keratinous material.

The examples below are given by way of illustration and with no limiting nature.

EXAMPLE 1

A nail-varnish-removing lotion having the following composition was prepared:

ethyl acetate 77.5 g
ethyl guar with a degree of substitution of about 2.5 (1) 4 g
glycerol 2 g
ethyl alcohol 12 g
water 4 g (1) sold under the name N-HANCE AG 200® by Aqualon A transparent lotion which removes a film of nail varnish easily was obtained.

EXAMPLE 2

A transparent make-up-removing lotion having the following composition was prepared:

acetone 83.5 g
ethyl alcohol 11 g
ethyl guar with a degree of substitution of about 2.5 (1) 4 g
glycerol 2 g (1) sold under the name N-HANCE AG 200® by Aqualon This slightly thickened, fluid lotion was suitable for removing make-up from the nails.

EXAMPLE 3

A make-up-removing oil having the following composition was prepared:

2-ethylhexyl palmitate 40 g
liquid petroleum jelly 10 g
apricot plant oil 10 g
ethyl guar with a degree of substitution of about 2.5 (1) 4 g
isononyl isononanoate qs 100 g (1) sold under the name N-HANCE AG 200® by Aqualon

We claim:

1. A process for removing make-up from nails comprising the step of contacting said make-up with a gel comprising at least one polysaccharide alkyl ether formed of units containing at least two different saccharide rings, wherein each unit contains at least one hydroxyl group substituted with a saturated hydrocarbon-based alkyl chain and a make-up-removing system comprising an effective amount of at least one component selected from non-aqueous solvents, said step of contacting being carried out under conditions sufficient to remove said make-up from said nails.

2. A process for removing make-up according to claim 1, wherein two to four hydroxyl groups per unit are substituted with said saturated hydrocarbon-based alkyl chain.

3. A process for removing make-up according to claim 1, wherein said saturated hydrocarbon-based alkyl chain contains from 1 to 24 carbon atoms.

4. A process for removing make-up according to claim 3, wherein said saturated hydrocarbon-based alkyl chain contains from 1 to 10 carbon atoms.

5. A process for removing make-up according to claim 4, wherein said saturated hydrocarbon-based alkyl chain contains from 1 to 6 carbon atoms.

6. A process for removing make-up according to claim 5, wherein said saturated hydrocarbon-based alkyl chain contains from 1 to 3 carbon atoms.

7. A process for removing make-up according to claim 3, wherein said hydrocarbon-based alkyl chain is selected from methyl, ethyl, n-propyl, isopropyl, n-butyl, isobutyl and tert-butyl and n-pentyl radicals.

8. A process for removing make-up according to claim 7, wherein said hydrocarbon-based alkyl chain is selected from methyl, ethyl, n-propyl, isopropyl, n-butyl, isobutyl and tert-butyl radicals.

9. A process for removing make-up according to claim 1, wherein said at least one polysaccharide alkyl ether has a weight-average molecular weight ranging from greater than 100,000 to 1,000,000.

10. A process for removing make-up according to claim 9, wherein said at least one polysaccharide alkyl ether has a weight-average molecular weight ranging from greater than 200,000 to 1,000,000.

11. A process for removing make-up according to claim 1, wherein said saccharide rings are selected from mannose, galactose, glucose, furanose, rhamnose and arabinose.

12. A process for removing make-up according to claim 1, wherein said at least one polysaccharide alkyl ether is an alkyl ether of a gum.

13. A process for removing make-up according to claim 12, wherein said gum is selected from gums which are overall nonionic.

14. A process for removing make-up according to claim 12, wherein said gum is selected from guar gum, carob gum, karaya gum and gum tragacanth.

15. A process for removing make-up according to claim 1, wherein said alkyl ether is alkyl galactomannan with a $C_1$ to $C_6$ alkyl chain.

16. A process for removing make-up according to claim 15, wherein said alkyl ether is alkyl galactomannan with a $C_1$ to $C_3$ alkyl chain.

17. A process for removing make-up according to claim 1, wherein said at least one polysaccharide alkyl ether is guar gum containing an ethyl chain with a degree of substitution ranging from 2 to 3.

18. A process for removing make-up according to claim 17, wherein said degree of substitution ranges from 2.5 to 2.8.

19. A process for removing make-up according to claim 1, wherein the weight ratio of said at least one component to said polysaccharide alkyl ether ranges from 5:1 to 1000:1.

20. A process for removing make-up according to claim 1, wherein said at least one polysaccharide alkyl ether is present in an amount ranging from 0.1 to 20% by weight relative to the total weight of said composition.

21. A process for removing make-up according to claim 20, wherein said at least one polysaccharide alkyl ether is present in an amount ranging from 2 to 8% by weight relative to the total weight of said composition.

22. A process for removing make-up according to claim 21, wherein said at least one polysaccharide alkyl ether is present in an amount ranging from 3 to 6% by weight relative to the total weight of said composition.

23. A process for removing make-up according to claim 1, wherein said non-aqueous solvent is selected from ketones, alcohols, glycols, short-chain esters, ethers, alkanes, cyclic aromatic compounds and aldehydes that are liquid at room temperature.

24. A process for removing make-up according to claim 1, wherein said non-aqueous solvent is selected from methyl ethyl ketone, ethyl acetate, methyl acetate, propyl acetate and butyl acetate.

* * * * *